United States Patent
Sauane et al.

(10) Patent No.: US 9,395,375 B2
(45) Date of Patent: Jul. 19, 2016

(54) METHOD OF TREATING SIGMA 1 RECEPTOR-EXPRESSING TUMORS WITH INTERLEUKIN 24

(71) Applicant: Research Foundation of the City University of New York, New York, NY (US)

(72) Inventors: Moira Sauane, New York, NY (US); Winchie Do, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 14/476,259

(22) Filed: Sep. 3, 2014

(65) Prior Publication Data

US 2015/0064239 A1 Mar. 5, 2015

Related U.S. Application Data

(60) Provisional application No. 61/873,144, filed on Sep. 3, 2013.

(51) Int. Cl.
*G01N 33/68* (2006.01)
*A61K 38/20* (2006.01)
*A61K 9/00* (2006.01)

(52) U.S. Cl.
CPC ............ *G01N 33/6869* (2013.01); *A61K 38/20* (2013.01); *A61K 9/0019* (2013.01); *G01N 2500/10* (2013.01)

(58) Field of Classification Search
CPC ... A61K 9/0019; A61K 31/713; A61K 38/20; A61K 48/00; G01N 33/6869; G01N 2500/10
See application file for complete search history.

(56) References Cited

PUBLICATIONS

Do W, et al. Biochem Biophys Res Commun. 439(2):215-20. Sep. 20, 2013. Available online at—doi: 10.1016/j.bbrc.2013.08.057. Epub Aug. 26, 2013.*
Spruce BA, et al. Cancer Res. 64; 4875-4886. Jul. 15, 2004. Available online at—doi: 10.1158/0008-5472.CAN-03-3180.*

* cited by examiner

*Primary Examiner* — Robert Landsman
(74) *Attorney, Agent, or Firm* — Peter J. Mikesell; Schmeiser, Olsen & Watts, LLP

(57) ABSTRACT

A method for identifying modulators of Interleukin 24 (IL-24) mediated apoptosis is disclosed. For IL-24 apoptosis to be effective, the cells should express Sigma 1 Receptor (S1R). Additionally apoptosis modulators can be identified by exposing biological cells to test compounds and monitoring for signs of endoplasmic reticulum (ER) stress protein expression; calcium mobilization; or reactive oxygen species (ROS) production.

10 Claims, 4 Drawing Sheets

METHOD OF TREATING SIGMA 1 RECEPTOR-EXPRESSING TUMORS WITH INTERLEUKIN 24

CROSS-REFERENCE TO RELATED APPLICATIONS

This application is a non-provisional of U.S. Patent Application Ser. No. 61/873,144 (filed Sep. 3, 2013) the entirety of which is incorporated by reference.

BACKGROUND OF THE INVENTION

The subject matter disclosed herein relates to a method of enhancing the effectiveness of Interleukin-24 (IL-24) cancer therapy.

An adenovirus expressing Interleukin-24, Ad.IL-24 (INGN 241), is known to exhibit activity by intratumoral injection in patients with advanced solid tumors. The use of Ad.IL-24 is safe and able to induce as much as 70% apoptosis in tumors after a single injection of recombinant virus and multiple injections generate clinical responses. Moreover, secreted IL-24 protein, generated from Ad.IL-24-infected cells, promotes antiangiogenic, immunostimulatory, radiosensitizing and "bystander" antitumor activities. IL-24 as a cancer gene therapeutic has several advantages over other candidate molecules, including high tumor cell specificity, anti-angiogenic properties, ability to radiosensitize, as well as cause growth-suppressive effects that are independent of p53, p16, Rb and BAX mutational status. In addition, IL-24 may be used in conjunction with existing p53-based therapeutics and has shown potential synergism with immuno- and chemo-therapy, potentially allowing a reduction in dose of all components in a given therapy. However, despite the extensive studies, questions remain about how IL-24 exerts its tumor-specific effect.

IL-24 is a member of the IL-10 family of cytokines. IL-24 binds to IL-20 receptor liccomplexes and activates TAT T signaling cascade. IL-24 possesses the properties of a classical cytokine as well as a tumor suppressor protein. When expressed at supraphysiological levels, by means of an adenoviral (Ad) expression system (Ad.IL-24), IL-24 induces growth suppression and apoptosis in a broad spectrum of human cancer cells, without exerting any deleterious effects on their normal counterparts. Furthermore, secreted IL-24 protein generated from Ad.IL-24 infection, induce cancer-specific apoptosis. Ad.IL-24 induces cancer-selective apoptosis even in the absence of JAK/STAT signaling. As evidenced by the expression of ER stress markers (BiP, CHOP, and phospho-eIF2a) Ad.IL-24 or secreted IL-24 protein, induce ER stress. Ad.IL-24 or secreted IL-24 protein also generates reactive oxygen species (ROS) in the mitochondria. Ad.IL-24 induces ceramide production in cancer cells. Adenovirus delivery of IL-24 inhibits f3-catenin and phosphatidylinositol 3'-kinase signaling pathways in lung cancer cells and activates Fas-FasL signaling in ovarian cancer cells. Infection of melanoma cells with Ad.IL-24 results in activation of death ligands (FasL), tumor necrosis factor-related apoptosis-inducing ligand (TRAIL), and their respective death receptor signaling pathways.

Secreted IL-24 protein has been shown to induce a robust expression of endogenous IL-24 and subsequent induction of tumor-specific killing through an ER stress-mediated pathway as well as by ROS production. IL-24 protein has been shown to induce stabilization of its own mRNA without activating its promoter. Ad.IL-24 has been shown to induce $p38^{MAPK}$. The $p38^{MAPK}$ has been shown to regulate IL-24 expression by stabilization of the 3'UTR of their mRNA. The ER stress pathway is believed to be the initial pathway in IL-24-induced apoptosis. IL-24 may cause ER stress by physically interacting with the ER chaperon protein BiP. IL-24:BiP binding might be mediated by the interaction of IL-24 with as yet unidentified protein that confers cancer cell specificity. The precise molecules mediating this pathway remain unclear. An improved method of IL-24 cancer therapy is therefore desired.

The discussion above is merely provided for general background information and is not intended to be used as an aid in determining the scope of the claimed subject matter.

BRIEF DESCRIPTION OF THE INVENTION

A method for identifying modulators of Interleukin 24 (IL-24) mediated apoptosis is disclosed. For IL-24 apoptosis to be effective, the cells should express Sigma 1 Receptor (S1R). Additionally apoptosis modulators can be identified by exposing biological cells to test compounds and monitoring for signs of endoplasmic reticulum (ER) stress protein expression; calcium mobilization; or reactive oxygen species (ROS) production. An advantage that may be realized in the practice of some disclosed embodiments of the method is that additional compounds that are functional equivalents of IL-24 may be identified. The present disclosure relates to the discoveries that apoptotic effects of IL-24 on malignant cells occur via Sigma 1 Receptor pathway. Accordingly, the disclosure provides methods for identifying apoptosis-modulating agents using assay(s) which determine the ability of a test agent to increase or decrease expression of constituents of the IL-24 apoptosis pathway. Such agents may be small molecules or may be fragments, variants and/or derivatives of native IL-24.

In a first embodiment, a method for identifying a compound capable of acting as a surrogate of Interleukin 24 (IL-24) by binding to Sigma 1 Receptor (S1R) intracellularly is provided. The method comprising steps of contacting a biological cell with a test compound, wherein the biological cell expresses S1R; determining whether diminished endoplasmic reticulum (ER) stress protein expression; calcium mobilization; or reactive oxygen species (ROS) production is produced, wherein the activation of ER stress, the mobilization of calcium or ROS production indicates that the test compound acts as a surrogate of IL-24, the step of determining being determined in comparison to a substantially identical biological cell that is not contacted with the test compound.

In a second embodiment, a method for identifying a compound for treatment hyperproliferative or autoimmune disorder by binding to Sigma 1 Receptor (S1R) is provide. The method comprising a step of coimmunoprecipitating a test compound with S1R, wherein the test compound is identified as useful for treatment hyperproliferative or autoimmune disorder if a precipitate is formed.

In a third embodiment, a method for treatment of a hyperproliferative or autoimmune disorder is provided. The method comprising steps of verifying a tumor sample of biological cells expresses Sigma 1 Receptor (S1R), wherein, if the tumor sample does express S1R, further comprising introducing a nucleic acid comprising Interleukin 24 (IL-24) into the tumor sample under conditions permitting expression of a gene that expresses IL-24 so as to induce apoptosis in the biological cell.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1A:
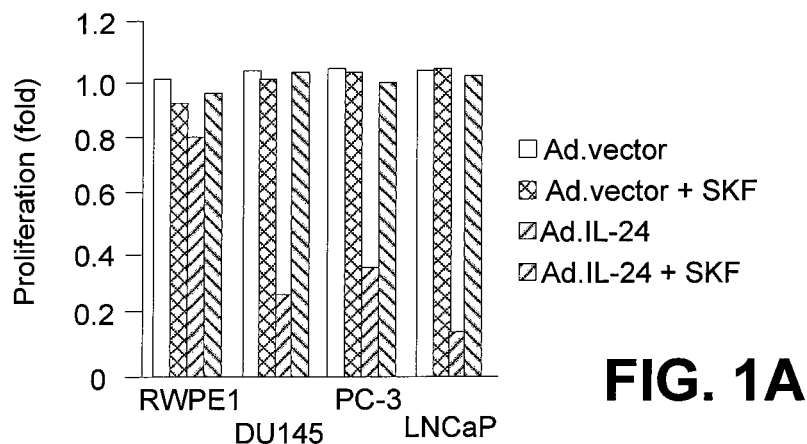
FIG. 1A, FIG. 1B and FIG. 1C are graphs depicting the effects of an S1R agonist on an Ad.vector or on AD-IL-24.

The present disclosure provides methods that utilize Sigma 1 receptor (S1R) in conjunction with Interleukin-24 (IL-24) to induce cell death. S1R, a ligand-regulated protein chaperone, has been shown to contribute to IL-24 induction of apoptosis. IL-24, a member of the IL-10 cytokine family, is an immunomodulatory cytokine that also displays broad cancer-specific suppressor effects. The tumor suppressor activities of IL-24 include inhibition of angiogenesis, sensitization to chemotherapy, and cancer-specific apoptosis. IL-24 generated from an adenovirus expressing IL-24 (Ad.IL-24) induces cancer-specific apoptosis by inducing an endoplasmic reticulum (ER) stress, reactive oxygen species production, and calcium mobilization.

Several lines of evidence are provided to confirm a physical and functional interaction between IL-24 and S1R including: (a) S1R and IL-24 co-localize, as judged by immunocytochemical analysis studies; (b) S1R and IL-24 co-immunoprecipitate using either S1R or IL-24 antibody; (c) S1R agonist (+)-SKF10047 inhibits apoptosis by Ad.IL-24; (d) (+)-SKF10047-mediated inhibition of Ad.IL-24 results in: diminished ER stress protein expression; (e) calcium mobilization; and (f) ROS production. Collectively, these data demonstrate that S1R interacts with IL-24 and suggest that IL-24:S1R interaction determines apoptosis induction by Ad.IL-24. The disclosure identifies S1R as an initial mediator of IL-24 induction of cancer-specific killing.

Sigma 1 Receptor (S1R)

S1R is a ligand-regulated protein chaperone. S1R is a receptor chaperone whose activity can be activated/deactivated by specific ligands. Manipulation of S1R can yield either cytoprotective or cytotoxic actions. The stimulation with sigma agonists induces S1R dissociation from BiP and S1R delocalization, while sigma ligands classified as antagonists impede this process. S1R agonists promote cellular survival by preventing oxidative stress caused by ischemia, diabetes, inflammation, and amyloid toxicity. Conversely, antagonists of the S1R inhibit tumor cell survival and induce apoptosis. Sigma antagonist-mediated cell death is inhibited by the prototypic sigma-1 agonists (+)-SKF10047. Furthermore, systemic administration of sigma antagonists significantly inhibits the growth of mammary carcinoma xenografts, prostate tumors, and lung carcinoma in the absence of side effects. On the other hand, several normal cell types such as fibroblasts, epithelial cells, and even sigma receptor-rich neurons are resistant to the apoptotic effects of sigma antagonists. Cellular susceptibility appears to correlate with differences in S1R coupling rather than levels of expression. In cancer cells only, sigma antagonists evoke a rapid rise in cytosolic calcium that is inhibited by S1R agonists. In tumor cells, sigma antagonists cause activation of phospholipase C and concomitant inhibition of phosphatidylinositol 3'-kinase pathway signaling.

This disclosure shows, for the first time, that S1R plays a decisive role in IL-24-mediated apoptosis. Several lines of evidence are provided to confirm a physical and functional interaction between IL-24 and S1R. These studies define S1R as a key initial mediator of IL-24. These findings have important implications for the understanding of IL-24 as a tumor suppressor protein as well as an immune modulating cytokine.

Treatment of cells with Sigma 1 receptor (S1R) agonist prevents IL-24 killing. Without wishing to be bound to any particular theory, IL-24 is believed to act as a S1R antagonist in mediating tumor cell death.

Figure 1B:
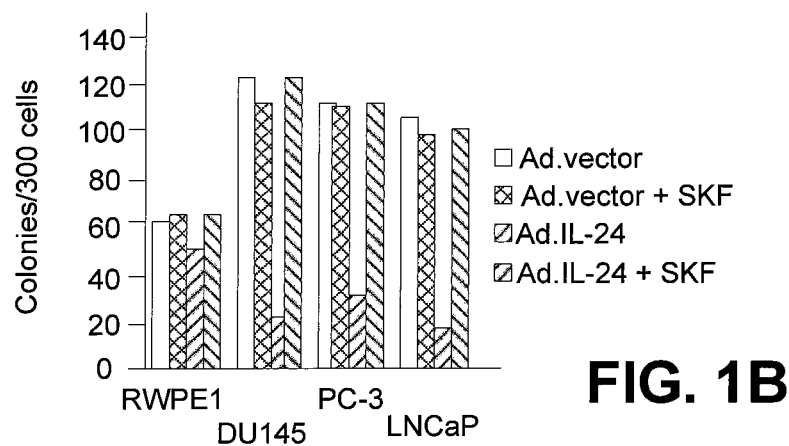
Figure 1C:
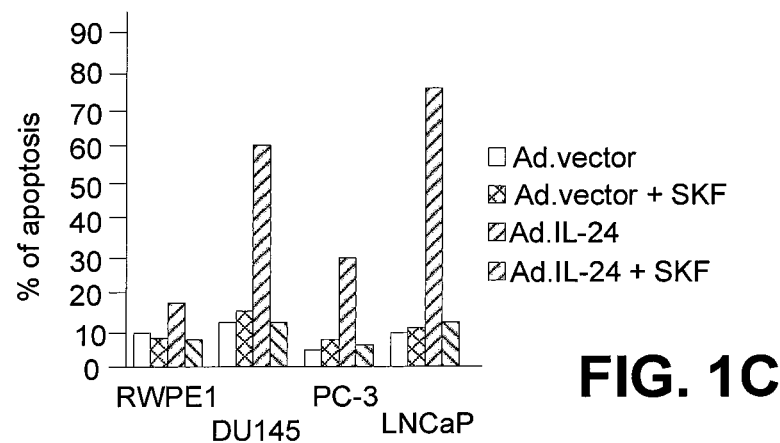

Referring to FIG. 1A, FIG. 1B and FIG. 1C, to test this hypothesis Ad.IL-24 was used to treat normal human immortalized epithelial cells (RWPE1), and three metastatic prostate cancer cell lines (LNCaP, DU145 and PC-3) in the presence or absence of the specific S1R agonist, (+)SKF-10047, and measured cell viability and induction of apoptosis by MTT, clonogenic, and AnnexinV-FITC/PI assays. (+)SKF-10047 inhibited Ad.IL-24-mediated killing in PC-3, LNCaP and DU145 cells. Ad.IL-24 had only a slight effect on viability, clonogenic capacity, or apoptosis of normal RWPE1 cells. The results show treatment of cells with a Sigma 1 receptor (S1R) agonist prevents IL-24-induced apoptosis.

In FIG. 1A, cells were infected with 100 pfu/cell of Ad.vector or Ad.IL-24, and treated with or without 10 μM (+)-SKF10047—a S1R agonist. Cell viability was determined by MTT assay 4 days post-infection. MTT absorbance of untreated control cells was set at 1 to determine relative number of viable cells. FIG. 1A shows the cytotoxic effect of Ad.IL-24 could be substantially negated by the addition of the S1R agonist. In FIG. 1B, cells were incubated in the absence or presence of 10 μM (+)-SKF10047 after infection with Ad.IL-24. Forty-eight hours post-infection, percentage of apoptosis was determined by staining with AnnexinV-FITC/

PI. FIG. 1B also shows the cytotoxic effect of Ad.IL-24 could be substantially negated by the addition of the S1R agonist. In FIG. 1C, cells were incubated in the absence or presence of 10 µM (+)-SKF10047 after infection with Ad.IL-24. Cells were subjected to clonogenic assay for 2 weeks. Results shown are an average of three independent experiments ±SD. FIG. 1C also shows the cytotoxic effect of Ad.IL-24 could be substantially negated by the addition of the S1R agonist. Taken together, the data of FIG. 1A, FIG. 1B and FIG. 1C suggest that IL-24-induced cell death in cancer cells would be achieved by antagonizing S1R, and is therefore inhibited by an S1R agonist.

Figure 2A:
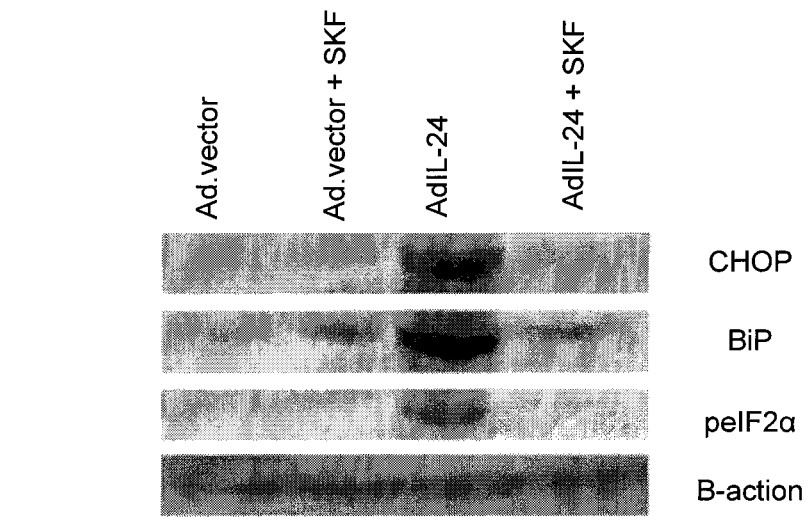
FIG. 2A is a Western blot analysis showing changes in BiP, CHOP, and p-eIF2a proteins after indicated treatments.
Figure 2B:
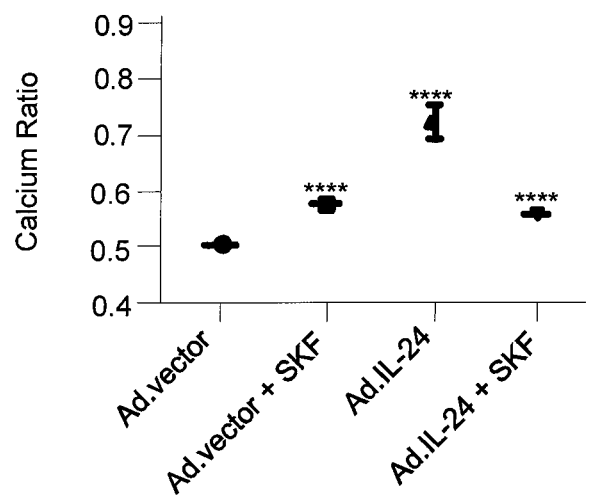
FIG. 2B depicts a ratio of calcium ratios for cells infected with Ad.vector or Ad.IL-24, with or without S1R agonist treatment.
Figure 2C:
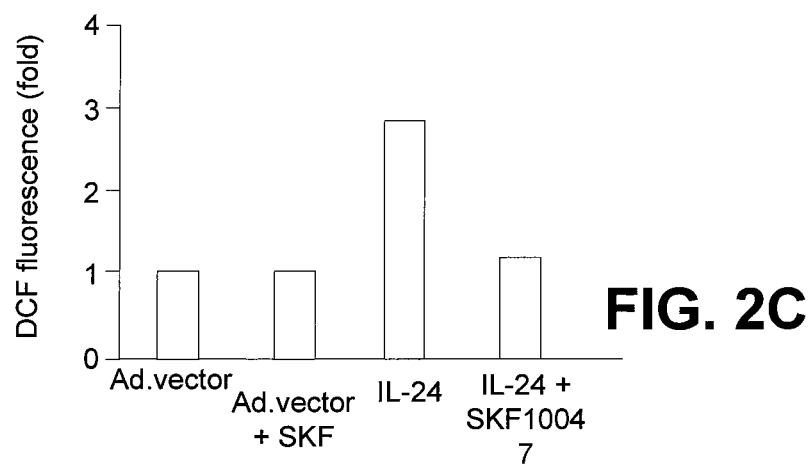
FIG. 2C graphically shows the fluorescence of cells infected with Ad.vector or with Ad.IL-24 and treated with or without a S1R agonist.

As shown in FIG. 2A, FIG. 2B and FIG. 2C, S1R is involved in Ad.IL-24-induced ER stress, calcium mobilization, and ROS production. Cells were infected with 100 pfu/cell of Ad.vector or Ad.IL-24, and treated with or without 10 µM (+)-SKF10047 (SKF) for indicated times. In FIG. 2A, changes in BiP, CHOP, and p-eIF2a proteins were evaluated by Western blot analysis 48 h after indicated treatments. FIG. 2A shows Ad.IL-24 infection causes IL-24 protein localization in the ER and induces ER stress resembling an UPR. Up-regulation by IL-24 of several ER stress markers is shown, including p-eIF2a, CHOP, and BiP, were inhibited by treatment with (+)SKF-10047.

FIG. 2B depicts a ratio of calcium ratios for cells infected with 100 pfu/cell of Ad.vector or Ad.IL-24, and treated with or without 10 µM (+)-SKF10047. The ratios are the levels cytosolic calcium at T=0 and T=12 hours. A determination was made concerning whether Ad.IL-24 caused any changes in the cytosolic levels of $Ca^{++}$ in prostate cancer cells and if $Ca^{++}$ mobilization is S1R-dependent after Ad.IL-24 infection. Ad.IL-24 infection increased cytosolic $Ca^{++}$ levels in prostate DU145 within 12 hours. The increase in $Ca^{++}$ was blocked by S1R agonist (+)-SKF10047.

FIG. 2C graphically shows the fluorescence of DU-145 cells infected with Ad.vector or with Ad.IL-24 and treated with or without 10 µM (+)SKF-10047 for 24 h. Intracellular ROS levels were measured with 10 µM DCF-DA 30 min after treatments. The results are expressed as the mean±S.D. of three independent experiments. The time course of mitochondrial changes (ROS generation) were determined after treatment of DU145 cells with Ad.IL-24. Cells were infected with Ad.IL-24, collected at 24 h, and stained for ROS production with dichlorofluorescin diacetate (DCFH-DA). FIG. 2C shows Ad.IL-24 increased ROS, were inhibited by treatment with (+)SKF-10047. Taken together, the inhibition by an S1R agonist of IL-24-mediated ER stress, $Ca^{++}$ mobilization and ROS production, further strengthen the hypothesis that IL-24 action in cancer cells is mediated by an antagonistic effect of IL-24 on S1R.

Figure 3A:
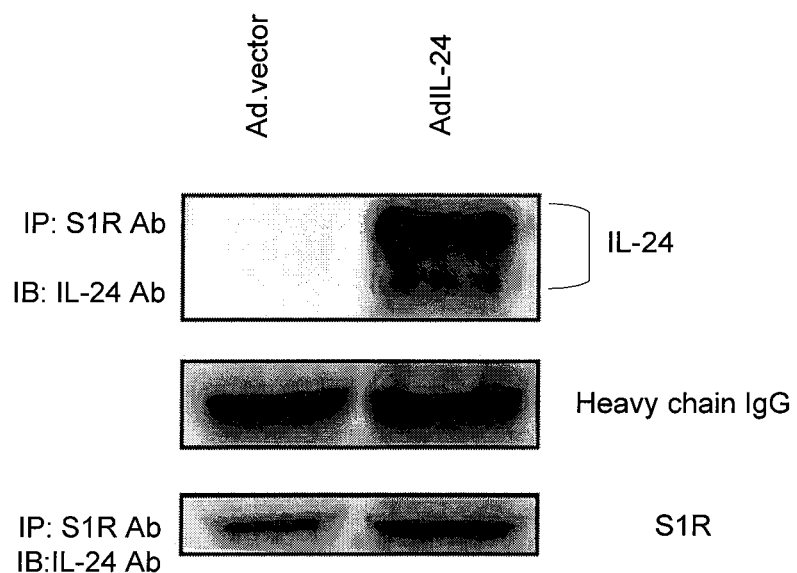
FIG. 3A and FIG. 3B depict comparative co-localizations of IL-24 and S1R proteins in cells after infection with the Ad.IL-24 virus.
Figure 3B:
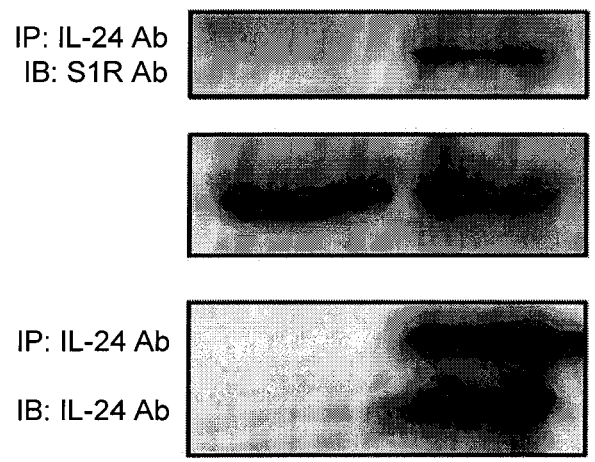

In FIG. 3A and FIG. 3B, comparative co-localization of IL-24 and S1R proteins was analyzed in DU145 cells after infection with the Ad.IL-24 virus. Comparison of the immunofluorescence data using different cells and secondary antibodies performed at independent times, yielded similar reproducible patterns of staining, demonstrating that IL-24 co-localized with S1R. DU-145 cells were infected with Ad.IL-24. After 24 h, cells were fixed and IL-24 and S1R proteins were detected by immunofluorescence using anti-IL-24 and anti-S1R antibodies. The analysis of co-localization of IL-24 and S1R was performed using a DMI6000B inverted confocal microscope with TCS SP5 system (Leica Microsystems CMS). Without wishing to be bound to any particular theory, S1R is believed to interact with IL-24.

Referring to FIG. 3A, infection with Ad.IL-24 followed by immunoprecipitation using anti-S1R antibody and immunoblotting with anti-IL-24 antibody confirmed a physical interaction between these molecules (FIG. 3A). In FIG. 3A, DU145 cells were infected with 100 pfu/cell of Ad.vector or Ad.IL-24 and immunoprecipitation analysis was done 48 hours later using S1R antibody.

As shown in FIG. 3B, experiments were also done in a reverse direction: immunoprecipitation was done using anti-IL-24 antibody and the membrane was probed with the anti-S1R antibody (FIG. 3B). IL-24 protein coimmunoprecipitated with S1R, demonstrating a physical interaction between these two molecules, converging with the above results in supporting the hypothesis that IL-24 could antagonize S1R. In FIG. 3B, DU-145 cells were infected with 100 pfu/cell of of Ad.vector or Ad.IL-24 and immunoprecipitation analysis was done 48 hours later using IL-24 antibody.

Figure 4:
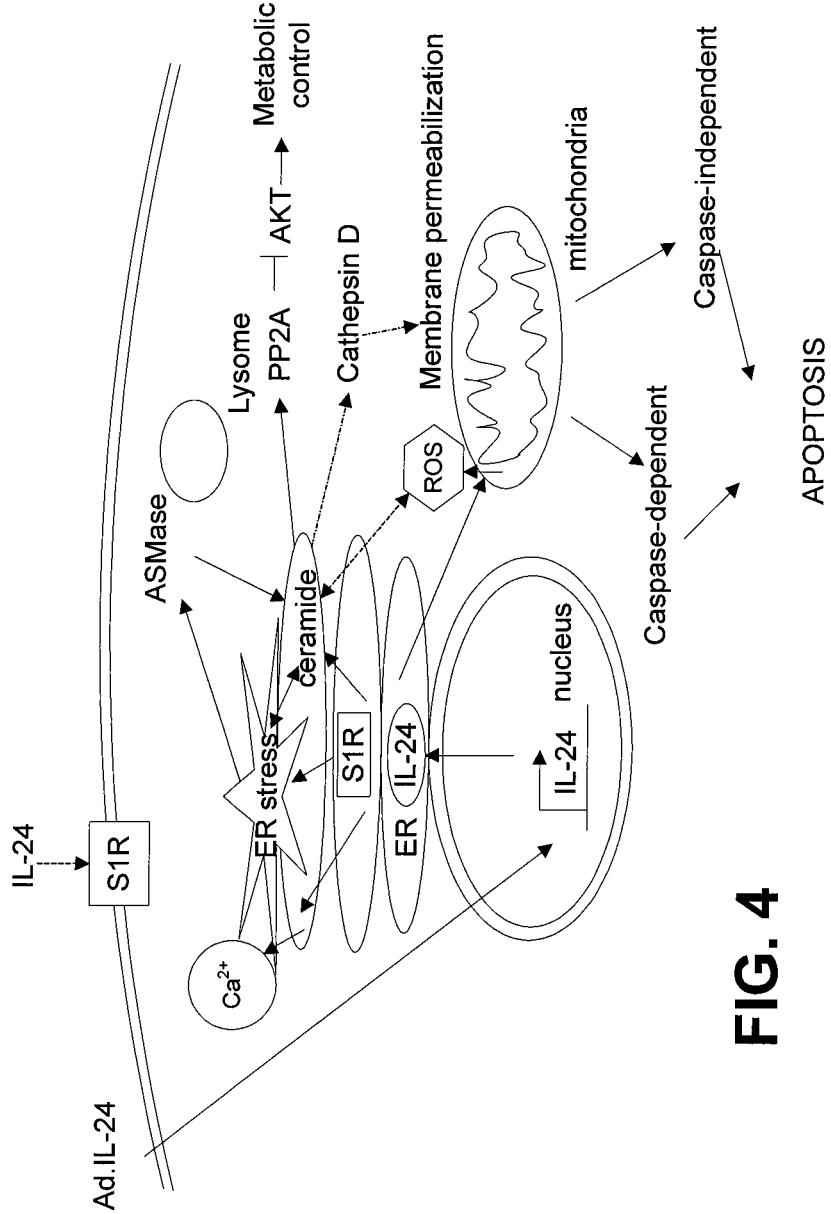
FIG. 4 depicts one possible method of operation.

Defining the biochemical basis of cancer-selective activity of IL-24 provides an important entry point for rationally devising combinatorial approaches to enhance the therapeutic impact of this intriguing multifunctional antitumor molecule. IL-24 displays a broad range of antitumor properties including cancer-specific induction of apoptosis, inhibition of tumor angiogenesis, and modulation of anti-tumor immune responses. The results presented here identify S1R as a key mediator of IL-24 induction of cancer-specific killing. S1R agonist (+) SK-10047 blocks Ad.IL-24-mediated cancer-selective apoptosis in prostate cancer cells (FIG. 1A, FIG. 1B, FIG. 1C). ER stress response, ROS production, and calcium mobilization triggered after Ad.IL-24 infection is mediated through a S1R-dependent pathway (FIG. 2A, FIG. 2B, FIG. 2C). Co-immunoprecipitation and co-localization studies revealed for the first time that IL-24 interacts with S1R (FIG. 3A, FIG. 3B). Ad.IL-24 induces apoptosis through a S1R antagonistic mechanism. IL-24 exerts a tumor-selective, ER stress, ROS production, calcium mobilization effect by acting through a S1R antagonistic mechanism. One possible mechanism of operation is shown in the model of FIG. 4 wherein IL-24 induces growth inhibition and apoptosis through a S1R-dependent pathway.

IL-24 induces ER stress and this response could be the common upstream event. Downstream targets of IL-24 after induction of ER stress include $p38^{MARK}$, calcium mobilization, ROS, and ceramide production. Ad.IL-24 induces ceramide production, and that plays a key role in ROS production, which in turn, can generate additional molecules of ceramide. IL-24 protein generates additional molecules of IL-24 that induce more ER-stress culminating in an untenable imbalance resulting in apoptosis in cancer cells.

Secreted IL-24 protein, generated from Ad.IL-24-infected cells, promotes antiangiogenic, immunostimulatory, radiosensitizing and "bystander" antitumor activities. IL-24 stimulates the immune system to generate secondary cytokines, such as TNF-a, IFN-y, and IL-1 that evokes an antitumor immune response. Secreted IL-24 protein, generated from Ad.IL-24-infected cells, exerts antiangiogenic activity by inhibiting endothelial cell differentiation and by blocking the activities of VEGF and TGF-a via inhibition of src activity within tumor cells. IL-24 protein generates additional molecules of IL-24 that induces more ER-stress culminating in an untenable imbalance resulting in apoptosis in cancer cells. Specifically, exogenous IL-24 protein induces growth inhibition and apoptosis only in cancer cells through a mechanism identical to Ad.IL-24 infection. These observations coupled with the present findings suggest that IL-24-mediated IL-24 induction could involve an S1R-mediated mechanism as an event down-stream of IL-20 receptor activation by extracellular IL-24. As discussed in the present work these findings have important implications for the understanding of IL-24 as a tumor suppressor protein as well as an immune modulating cytokine. In accordance with what has been observed with IL-24, the combination of immunosuppression, along with anti-inflammatory properties makes S1R ligands attractive molecules for therapeutic applications such as autoimmune diseases in which both immune and inflammatory disorders are involved. Interestingly, S1R to translocate and remodel the plasma membrane. Accumulating evidence indicate that S1R is overexpressed in many cancer cell lines, and contributes to the invasion and metastasis in many human tumors.

This disclosure support the hypothesis that Sigma 1 Receptor (S1R) may be the upstream initial signal transduction molecule common to these cascades of events involving IL-24-induced ER-stress dependent and independent downstream pathways. In summary, the identification of S1R as a mediator of IL-24-cancer-specific apoptosis significantly broadens their therapeutic potential for tumors as well as provides new important knowledge for the understanding of IL-24 as an immune modulating cytokine.

Materials and Methods

Virus infection. The IL-24 expressing replication defective Ad.IL-24 and corresponding empty adenovirus vector lacking exogenous gene, used as a control (Ad.vector) were custom engineered by Vector Biolabs, Inc. (Philadelphia, Pa.).

Cells and culture conditions. RWPE1, LNCaP, DU145, and PC3 (ATCC, Rockville, Md.) cell lines were grown in DMEM with 10% fetal bovine serum (FBS) 1% penicillin/streptomycin. All cell lines were cultured in humidified atmosphere at 37° C. with 5% $CO_2$ and media was replaced every alternate day. (+)-SKF10047 was purchased from Tocris (Tocris, UK).

Western Blot Analysis. Protein extracts were prepared with RIPA buffer containing a mixture of protease inhibitors as described in Sauane M, Su Z Z, Dash R, et al. "Ceramide plays a prominent role in MDA-7/IL-24-induced cancer-specific apoptosis" J Cell Physiol. 2010 March; 222(3):546-55. Fifty micrograms of protein was applied to a 12% SDS/PAGE and transferred to nitrocellulose membranes. The membranes were probed with polyclonal or monoclonal antibodies to IL-24, p-eIF2a, BiP, CHOP, Sigma 1 Receptor, and beta-actin.

MTT Assays. Cells were plated in 96-well dishes ($1\times10^3$ cells/well) in DMEM containing 10% FBS and allowed to attach for 12 h prior to treatment(s). Inhibitors were added 4 h after infection with adenovirus. Cell growth and viable cell numbers were monitored by 3-(4,5 dimethylthiazol-2-yl)-2, 5-diphenyltetrazolium bromide (MTT) staining as described in Sauane M, Su Z Z, Dash R, et al. "Ceramide plays a prominent role in MDA-7/IL-24-induced cancer-specific apoptosis" J Cell Physiol. 2010 March; 222(3):546-55.

Annexin V binding assays. Cells were trypsinized, washed once with complete medium and PBS, resuspended in 0.5 ml of binding buffer containing 2.5 mmol/L $CaCl_2$, and stained with allophycocyanin-labeled Annexin V (Becton Dickinson Biosciences, Palo Alto, Calif.) and propidium iodide (PI) for 15 min at room temperature. Flow cytometry assays were performed as described in Sauane M, Su Z Z, Dash R, et al. "Ceramide plays a prominent role in MDA-7/IL-24-induced cancer-specific apoptosis" J Cell Physiol. 2010 March; 222 (3):546-55.

Colony formation assays. Cells were infected with 100 pfu/cell with Ad.vector or Ad.IL-24. The next day, 200 to 500 cells were seeded to determine colony-forming ability. After 2 weeks of incubation, colonies were fixed, stained with 5% Giemsa solution, and colonies of >50 cells were enumerated as described in Sauane M, Su Z Z, Dash R, et al. "Ceramide plays a prominent role in MDA-7/IL-24-induced cancer-specific apoptosis" J Cell Physiol. 2010 March; 222(3):546-55.

Immunofluorescence. Cells were seeded onto chamber slides (Falcon; BD Biosciences, San Jose, Calif.) and maintained in DMEM with 10% fetal bovine calf serum, 24 hours postinfection, cells were fixed with 2% paraformaldehyde, permeabilized by 0.1% Triton X-100, and then incubated with primary antibodies: IL-24, and S1R. Controls were incubated with only the secondary antibodies under the same experimental conditions.

Co-immunoprecipitation of S1R with IL-24. Cells were infected with Ad.vector or Ad.IL-24. After 48 hours, protein was extracted from subconfluent cultures using lysis buffer (Pierce, Rockford, Ill.) containing 1 mM phenylmethlsulfonylfluoride (Sigma-Aldrich, Inc) and quantified using the BCA protein assay kit (Pierce, Rockford, Ill.). Antibodies were conjugated to Protein-G beads according, the Sigma Protein-G Immunoprecipitation Kit manufacturer's instructions (Sigma-Aldrich, Inc). Western blot analysis was done as described before using the following primary antibodies at 1:1,000 dilutions: anti-IL-24, and anti-S1R. Secondary antibodies specific for heavy chain of immunoglobulin G (IgG) were used as the light chain of IgG interfered with detection of IL-24 because of similar size.

Calcium imaging. For Calcium ($Ca^{++}$) imaging, cells were plated in 35 mm glass bottom petri dishes (MatTek) and allowed to attach for 12 h prior to treatment(s). Inhibitors were added 4 h after infection with adenovirus. After 12 h, cells were then rinsed with a Ringer's solution maintained at 37° C. Cells were then incubated in Ringer's solution containing 0.5 µM Fura-2 tetra-acetoxymethyl ester (Fura-2) (Molecular Probes), 10% Pluronic F127 and 250 µm sulfinpyrazone (Sigma-Aldrich, Inc) for 40 min at 22° C. Fura-2 was excited by alternating 340 and 380 nm light and images were obtained every 50 ms as a measure of $Ca^{++}$ concentration. Background intensity was zero. A bolus injection brought the stimulant concentration in the cell bath to either 1 mM glutamate (Sigma-Aldrich, Inc) or 1 mM N-methyl-d-aspartic acid plus the co-stimulator 1 mM glycine. Prism Software (GraphPadVare Inc version 6.0C) was used to analyze the results. Intra-group analysis was done with ordinary one-way ANOVA to compare the mean of raw calcium ratios of each treatment group with a control group. A Dunnet's multiple comparison test with a single pooled variance was also performed on the four treatment groups. A significance of 0.01 was used in the analysis.

Assessment of reactive oxygen species (ROS) generation. DU-145 cells were seeded in 96-well plates at a concentration of $1\times10^4$ cells/well and were infected with Ad.IL-24 for 12 h. The cell cultures were treated with 10 µM 2,7-dichloro-fluorescein diacetate (DCFH-DA; Sigma-Aldrich, St. Louis, Mo.) in PBS for 30 min After incubation, the media was discarded, and the cells were washed with PBS. The fluorescence intensity was determined using a fluorescence plate reader at 485 nm for excitation and 530 nm for emission.

In one embodiment, a method for treatment of a hyperproliferative or autoimmune disorder is provided. Examples of hyperproliferative and/or autoimmune disorders include various cancers, including, breast, lung, ovarian, liver, pancreatic, gliomas, gastric, colorectal, renal, prostate human cancers etc. Examples of autoimmune disorders include treatment of keloid lesions, rheumatoid arthritis and spondyloarthropathy, inflammatory bowel disease etc. The tumor suppressor activities include inhibition of angiogenesis, sensitization to chemotherapy, and induction of cancer-specific apoptosis.

The method comprising steps of introducing a nucleic acid comprising Interleukin 24 (IL-24) into a biological cell under conditions permitting expression of the gene so as to thereby induce apoptosis in the biological cell. In one embodiment, a tumor sample is first verified to expresses Sigma 1 Receptor (S1R). If the tumor sample is positive for S1R expression, then IL-24 can be effective. If the tumor sample is negative for S1R expression, then IL-24 will not be effective.

In one embodiment, the nucleic acid is introduced into the biological cell via naked DNA technology using histone-free DNA.

In one embodiment, the nucleic acid is introduced into the biological cell via an adenovirus vector, an adeno-associated virus vector, an Epstein-Barr virus vector, a Herpes virus vector, an attenuated HIV vector, a retroviral vector, or a vaccinia virus vector.

In one embodiment, the nucleic acid is introduced into the biological cell via a liposome or an antibody-coated liposome.

In one embodiment, the nucleic acid is introduced into the biological cell via a means for mechanically introducing nucleic acids. Examples of means for mechanically introducing include microinjection of nucleic acids.

In one embodiment, the nucleic acid is introduced into the biological cell via means for electrically introducing nucleic acids. Examples of means for electrically introducing include electroporation and electropermeabilization.

In one embodiment, the nucleic acid comprises a vector, an adenovirus vector, a replication-defective adenovirus vector expressing mda-7, an adeno-associated virus vector, an Epstein-Barr virus vector. In one such embodiment, the vector is a Herpes virus vector, an attenuated HIV vector, a retrovirus vector, or vaccinia virus vector.

In one embodiment, the nucleic acid is linked to a cytomegalovirus promoter, or a eRSV) promoter.

In another embodiment, a method for identifying a compound capable of acting as a surrogate of IL-24 by binding to Sigma 1 Receptor intracellularly is provided. The method comprising steps of contacting a biological cell with a test compound, wherein the biological cell expresses Sigma 1 Receptor; determining whether diminished endoplasmic reticulum (ER) stress protein expression; calcium mobilization; or reactive oxygen species (ROS) production is produced, wherein the activation of ER stress, the mobilization of calcium or ROS production indicates that the test compound acts as a surrogate of IL-24.

In another embodiment, a composition of matter for treatment of a hyperproliferative or autoimmune disorder is provided. The composition of matter comprising Interleukin 24 (IL-24) and Sigma 1 Receptor (S1R), wherein the composition of matter is in a form of a controlled dosage form. Examples of controlled dosage forms including, one part injectables, two part injectables, oral dosage forms, adhesive pads, time release compositions, and the like.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for treating a tumor that expresses Sigma 1 Receptor (S1R), the method comprising steps of:
    (a) verifying a tumor expresses Sigma 1 Receptor (S1R), wherein, if the tumor does express S1R, further comprising:
    (b) introducing a nucleic acid comprising Interleukin 24 (IL-24) into the tumor under conditions permitting expression of a gene that expresses IL-24 so as to induce apoptosis in the tumor.

2. The method of claim 1, wherein the nucleic acid is introduced into the tumor via naked DNA technology.

3. The method of claim 1, wherein the nucleic acid is introduced into the tumor via an adenovirus vector, an adeno-associated virus vector, an Epstein-Barr virus vector, a Herpes virus vector, an attenuated HIV vector, a retroviral vector or a vaccinia virus vector.

4. The method of claim 1, wherein the nucleic acid is introduced into the tumor via a liposome or an antibody-coated liposome.

5. The method of claim 1, wherein the nucleic acid is introduced into the tumor via a means for mechanically introducing nucleic acid.

6. The method of claim 5, wherein the means for mechanically introducing nucleic acid is microinjection.

7. The method of claim 1, wherein the nucleic acid is introduced into the tumor via a means for electrically introducing nucleic acid.

8. The method of claim 1, wherein the nucleic acid is linked to a cytomegalovirus promoter.

9. The method of claim 1, wherein the nucleic acid comprises a vector.

10. The method of claim 9, wherein the vector is selected from the group consisting of an adenovirus vector, a replication-defective adenovirus vector expressing mda-7, an adeno-associated virus vector, an Epstein-Barr virus vector, a Herpes virus vector, an attenuated HIV vector, a retrovirus vector and a vaccinia virus vector.

* * * * *